United States Patent [19]

Hale

[11] Patent Number: 5,004,532
[45] Date of Patent: Apr. 2, 1991

[54] AMPEROMETRIC CELL

[75] Inventor: John M. Hale, Meinier, Switzerland

[73] Assignee: Orbisphere Corporation, Switzerland

[21] Appl. No.: 31,222

[22] Filed: Mar. 27, 1987

Related U.S. Application Data

[63] Continuation of Ser. No. 743,155, Jun. 10, 1985, abandoned.

[51] Int. Cl.$^5$ .............................................. G01N 27/40
[52] U.S. Cl. .................................. 204/415; 204/153.17
[58] Field of Search ..................... 204/1 P, 415, 153.17

[56] References Cited

U.S. PATENT DOCUMENTS

| | | | |
|---|---|---|---|
| 3,334,039 | 8/1967 | Vlasak | 204/415 |
| 3,410,778 | 11/1968 | Krasberg | 204/415 |
| 3,509,034 | 4/1970 | Paine | 204/415 |
| 3,575,836 | 4/1971 | Sternberg | 204/415 |
| 3,655,546 | 4/1972 | Marovich et al. | 204/415 |
| 4,092,232 | 5/1978 | Zetter | 204/415 |
| 4,096,047 | 6/1978 | Hale et al. | 204/415 |
| 4,132,616 | 1/1979 | TAntram et al. | 204/415 |
| 4,324,632 | 4/1982 | Vlasak | 204/415 |
| 4,325,797 | 4/1982 | Hale et al. | 204/415 |
| 4,372,021 | 2/1983 | Hale et al. | 29/235 |
| 4,435,268 | 3/1984 | Martin et al. | 204/415 |
| 4,474,648 | 10/1984 | Tantram et al. | 204/415 |
| 4,518,477 | 5/1985 | Wright et al. | 204/415 |
| 4,563,249 | 1/1986 | Hale | 204/415 |

Primary Examiner—T. Tung
Attorney, Agent, or Firm—Wigman & Cohen

[57] ABSTRACT

A membrane-enclosed amperometric cell (MEAC) for use in determining the concentration of an electroactive species of interest (EASI) in an ambient medium comprises: a working electrode defined by a periphery; a liquid electrolyte covering the sensing area in a film of uniform thickness and being in electrolytic contact with a counter eletrode; a flexible polymer membrane of generally uniform thickness that is substantially impermeable to the electrolyte but permeable to the EASI; the membrane extends in a substantially conforming manner over the sensing area and the electrolyte film thereon; the cell of the invention has a physical permeation barrier that (1) consists of a layer of a substantially inert solid material which is substantially impermeable to the electrolyte and to the EASI; (2) extends between the ambient medium and the sensing area; (3) is disposed in a parallel configuration and in physical contact with the membrane; (4) has at least one opening permitting access of the EASI through the membrane to the sensing area yet phsyically restricting such access to a limited portion of the sensing area; (5) the limited portion is enclosed by a circumjacent margin that has an outer periphery defined by the periphery of the sensing area, an inner periphery, and a width defined by the smallest distance between the outer and the inner periphery; and (6) the width of the circumjacent margin is at least three times greater than the thickness of the electrolyte layer, or at least three times greater than the thickness of the membrane, depending upon the position of the barrier.

4 Claims, 2 Drawing Sheets

AMPEROMETRIC CELL

This is a continuation of application Ser. No. 06/743,155, filed June 10, 1985, now abandoned.

CROSS-REFERENCE TO RELATED CASES

This application generally relates to subject matter disclosed in the following U.S. Applications:

U.S. application Ser. No. 773,163, filed Mar. 1, 1977, issued as U.S. Pat. No. 4,096,047; U.S. application Ser. No. 164,291, filed June 30, 1980, issued as U.S. Pat. No. 4,325,797; U.S. application Ser. No. 319,708, filed Nov. 9, 1981, issued as U.S. Pat. No. 4,372,021; U.S. application Ser. No. 345,536, filed Feb. 3, 1982, issued as U.S. Pat. No. 4,518,477, and U.S. application Ser. No. 493,316, filed May 10, 1983, now U.S. Pat. No. 4,563,249.

BACKGROUND OF THE INVENTION (a) Field of the Invention

This invention relates generally to the art of amperometric analysis and to devices of the type used for quantitative electrochemical determination of the concentration of an electroactive species of interest (herein called EASI) in an ambient medium; more particularly, this invention relates to an improved membrane-enclosed amperometric cell for use in such methods.

(b) Description of the Prior Art

Electrochemical cells for quantitative electrochemical analysis are well known in the art and generally include a working or sensing electrode having a generally flat and frequently circular sensing area covered by a thin film of a liquid electrolyte that extends into an electrolyte reservoir and is in electrolytic contact with a counter electrode; a flexible polymer membrane that is substantially impermeable to the electrolyte but permeable to the EASI (generally called "semipermeable") extends in a substantially conforming manner over the sensing area of the working electrode as well as the electrolyte film thereon. Such a "membrane-enclosed amperometric cell" will be called a MEAC hereinafter.

For amperometric analytical operation, the working electrode of such a MEAC is polarized by a constant DC voltage to furnish a current whose steady state magnitude is proportional to the activity of the EASI. Such MEAC's, their operation, and their use for determination purposes are discussed in the following illustrative U.S. Pat. Nos. 2,913,386, 4,096,047, 4,325,797 and in British Specification No. 2,013,895.

Structural and operational data of such prior art cells used for oxygen sensing are to be found in the literature, particularly in the Monography by Hitchman, Michael L., "Measurement of Dissolved Oxygen", John Wiley & Sons, Inc. and Orbisphere Laboratories, 1978.

While elemental (molecular or $O_2$) oxygen is a preferred EASI, others are of interest here as well and include elements or compounds that are more easily oxidized or reduced in the cell than the electrolyte (solvent and solvate); elemental hydrogen is another preferred EASI if measurement is made in line with the method disclosed in the above cited U.S. Ser. No. 493,316. The ambient medium may be gaseous or liquid and will generally contain the EASI in an essentially pure form or in an admixed or in a dissolved state, the EASI concentration varying between 100% and parts per million(ppm) or parts per billion ($10^{-9}$).

Depending upon whether the EASI are of the electroreducible type, such as oxygen, or of the electrooxidizable type, such as hydrogen, the sensing or working electrode of the MEAC will be the cathode or the anode, respectively, while the counter electrode will be the complementing electrode and suitable insulator means, i.e. non-metallic, inorganic or organic solids, are provided between the electrodes so that any current which is permitted to pass from the sensing electrode to the counter electrode is a ionic current in the electrolyte arising from electrochemical phenomena at the electrolyte-exposed electrodes.

For operation of a MEAC, the semipermeable membrane will be secured on the cell after the electrolyte-receiving portion including the sensing area of the working electrode is provided with the electrolyte which will be exchanged with the membrane for maintenance.

That portion of the EASI-exposed surface of the membrane in operative position and separating the ambient medium from the electrolyte is also called the "sensing face" of the MEAC; frequently, the sensing face will be a transverse and generally circular front face of an elongated tubular housing or jacket onto which the membrane is fastened. Normally, the housing or jacket material will be substantially impermeable to the EASI and the electrolyte-backed membrane portion should be the only part of the MEAC where the EASI can get into the electrolyte film or layer on top of the sensing area of the working electrode.

It will be appreciated that the electrolyte-covered and membrane-covered "sensing area" of the working electrode will generally be an essential and frequently central but not necessarily predominant portion of the membrane-covered "sensing face" of the MEAC.

The particular importance of the electrolyte film on top of the sensing area of the working electrode and the accessibility of this film to EASI will be explained in more detail below.

When measuring the concentration of an EASI in a fluid medium that contacts the sensing face of the MEAC, the desired current contribution normally originates from diffusion of the electroactive species directly through the membrane onto the sensing area of the working electrode and the corresponding electrochemical reaction of the EASI on the working electrode. In practice, however, additional and undesirable current contributions, i.e. those unrelated to the concentration of the electroactive species of interest in the medium, are observed and limit both accuracy and sensitivity of the measuring system, aside from causing problems of stabilization of the transient signal, stability of the steady state signal, undesired noise signals, and prolonged response time.

One specific type of undesirable current contributions is that caused by electrolyte penetration into the interface between the working electrode and the adjacent insulator portion as set forth by Applicant in the above cited U.S. Pat. No. 4,096,047 (incorporated herein by reference) and disclosing means to avoid such penetration by pressure sealing instead of conventional cementing.

Further research has shown that a predominant portion of the undesirable current contributions is due to diffusion and leakage effects. For example and with reference to the oxygen or hydrogen measurement as typical examples, the EASI may penetrate into the electrolyte remote from the sensing area of the electrolyte, e.g. via the membrane/housing junction, a housing-/electrode junction, an electrode/insulator junction, etc. These EASI constitute an "impurity" in the system and tend to diffuse "laterally" from the electrolyte space or reservoir into the electrolyte film on top of the sensing area of the working electrode where they will react and cause a current not related to the concentration of the EASI in the ambient medium that is in contact with the membrane surface directly adjacent the sensing area of the electrode. EASI diffusion or leakage into electrolyte portions other than the film on the sensing area of the working electrode and subsequent lateral diffusion into said film would thus be the primary cause of these undesired current contributions. However, when attempting, for example, a sensitivity of the amperometric oxygen detection from the parts per million [$10^{-6}$] (ppm) range into the parts per billion [$10^{-9}$] (ppb) range it is apparent that there is a limit to materials and structures that would be required for complete elimination of EASI leakage.

To the best knowledge of Applicant, the most effective prior art method for avoiding undesired current contribution caused by EASI leakage or undesired diffusion is to provide a third electrode commonly called a "guard" as disclosed, for example, in the above cited British Specification 2,013,895 and acting as an electric barrier against lateral diffusion of EASI onto the working electrode as explained below.

However, when working with advanced hydrogen determination methods as disclosed in the above cited U.S. Ser. No. 493,316 (incorporated herein by reference) it was found that even a guard electrode cannot eliminate all undesired current contributions in that—for example—an organic insulator between the working electrode and the guard may cause a residual current after hydrogen exposure of the MEAC because of the high solubility of hydrogen in most organic polymers so that the hydrogen dissolved or otherwise retained by this or another component of the MEAC will continue, for some time, to cause an undesired current contribution.

OBJECTS AND SUMMARY OF THE INVENTION

Accordingly, it is a primary object of this invention to provide for a MEAC with a novel and improved barrier means against undesired current contributions.

A further important object of the invention is a MEAC having a physical, i.e. a bodily and not an electrical, barrier that effectively prevents undesirable lateral diffusion of EASI into and through the electrolyte film on top of the sensing electrode and generally provides for shortening of the response time.

Another object of the invention is an improved MEAC for hydrogen sensing.

Yet a further object of the invention is an improved method for quantitative electroanalytical determination of EASI, both of the electroreducible type, such as oxygen, as well as of the electrooxidizable type, such as hydrogen.

Another object of the invention is to provide a detector for quantitative electroanalytical determination of EASI, dissolved in a liquid medium, of which the output signal is substantially independent of agitation or flow of the medium.

Further objects will become apparent as this specification proceeds.

The above objects and further advantages will be achieved according to the invention in a MEAC that comprises:

(A) a working or sensing electrode having a sensing area typically consisting of a noble metal, such as gold or platinum and alloys thereof, as well as stainless steel and other oxidation-resistant metals; the working electrode will be the cathode when measuring electroreducible EASI, such as oxygen, or the anode when measuring electrooxidizable EASI, such as hydrogen; preferably, the sensing area of the working electrode is generally flat, e.g. substantially planar or spherical with a large diameter of curvature of typically above 50 mm; the sensing area is defined by its periphery which, preferably, circumscribes a circle but may circumscribe another regular or irregular curved or polygonal shape. For many purposes it is preferred that the surface of the sensing electrode is smooth, e.g. polished to mirror brightness, as defined in the above mentioned U.S. Ser. No. 493,316. The size of the sensing area can vary as needed and is typically in the range of from about 5 to 100 mm$^2$.

Further, it will be preferred for many purposes that the sensing area of the working electrode is coaxial and concentric with a generally longitudinal and overall cylindrical cell structure, the electrode sensing area and the sensing face of the cell then being part of a "front face" arranged transversely to the longitudinal axis of the overall cell structure. For brevity and clear distinction, the sensing area of the working electrode will also be referred to herein as "sensing area (A)".

(B) A film of a liquid electrolyte in substantially uniform thickness of typically between about 5 and 50 $\mu$m (0.2–2 mil) covers the sensing area of the working electrode is in electrolytic contact, generally via an electrolyte space or reservoir, with a counter electrode which, in general, is "consumable" and will be oxidized or reduced depending upon the reaction at the sensing electrode and the corresponding counter reaction.

Counter electrodes made of silver and/or silver oxide are but typical examples.

(C) A flexible polymer membrane having a generally uniform thickness of typically in the range of from 10 to 300 $\mu$m (0.5 to 12 mil) or more and being substantially impermeable to the electrolyte but permeable to the EASI is provided to extend in a generally conforming manner over the sensing area of the working electrode and the electrolyte film thereon.

Normally, the electrolyte film on the sensing area will be shaped by the flexible membrane when the cell end is provided with a slight excess of electrolyte and the membrane is layed upon the electrolyte and pressed (conformingly) onto the cell end; then, the membrane is normally secured to the cell housing by conventional means, e.g. O-rings or, preferably, by a dye-ring as disclosed in U.S. Pat. No. 4,372,021.

Many examples of suitable materials for flexible polymer membranes are disclosed in the above cited patents and patent applications; a representative example of a flexible polymer membrane for oxygen measurement is PTFE (polytetrafluoroethylene) with a thickness of from 10 to 50 $\mu$m; for hydrogen measurement, a representative example of a suitable membrane is PVDC (polyvinylidene chloride).

Membrane thickness may be a means to control cell operation as explained in the above mentioned U.S. Ser. No. 493,316 or may be caused by a compromise between quick response and mechanical strength.

According to the present invention the MEAC includes as a further critical feature (D) a physical (i.e. bodily or mechanical) permeation barrier that satisfies the following essential requirements:

(D-1) It consists of a layer (also termed "barrier layer" herein) of a substantially inert (as regards the ambient medium, the electrolyte and the operating conditions) solid material that is substantially impermeable not only to the liquid electrolyte but also to the EASI; specific examples of suitable materials for the barrier layer will be given below but it should be understood that the term "substantially impermeable to the EASI" may depend upon the nature of the EASI and the thickness of the barrier layer since, for example, elemental hydrogen will permeate through such materials as metal sheeting so that the criterion "substantial impermeability to EASI" is best expressed in relation to the permeability of the semipermeable membrane of the MEAC when tested under the same conditions (thickness, temperature, pressure, etc.); hence, the barrier layer must in any case be substantially less permeable to the EASI than the semipermeable membrane when measured under identical conditions, typically by a factor of at least 10 and generally by a factor of at least 100 or more. For example, the semipermeable membrane must permit permeation of the EASI at a rate that is at least ten times and generally at least a hundred times greater than the corresponding rate of permeation of the EASI through the barrier layer.

(D-2) Further, the barrier layer must extend between said ambient medium and the sensing area and (D-3) be disposed in a substantially parallel configuration with the semipermeable membrane and be in physical contact with that membrane.

The conditions (D-2) and (D-3) may be satisfied either with an "external" or with an "internal" barrier, i.e. a barrier at the "outside" of the membrane (=the membrane surface in contact with the ambient medium but not with the electrolyte film) or at the "inside" of the membrane (=the membrane surface in contact with the electrolyte film but not with the ambient medium); they will not be met, however, by a barrier layer distanced from the membrane by a gap; generally, the mutually contacting surfaces of the barrier layer and the semipermeable membrane will be in a "sealing engagement" meaning that a continuous layer of a liquid would not form at the interface.

Such sealing engagement between the membrane and the barrier layer may be obtained by continuous pressure, by means of an adhesive or by adhesion depending upon the surface qualities of the membrane and the barrier layer; generally, such sealing engagement will not present a problem because most polymer membranes for use with MEAC's will exhibit surface sealing qualities even at low specific contact pressures.

For example, a typical external barrier suitable for use with all types of EASI is an essentially flat metal sheet (typical gauge of 50–2000 μm) made of stainless steel and maintained in pressing engagement with the flexible polymer membrane by means of a clamp, bracket or the like. Such clamp-induced pressure of the steel sheet barrier layer against the membrane covering an essentially flat electrode sensing area will normally be sufficient for a sealing engagement of barrier and membrane in line with criterion (D-3).

(D-4) The permeation barrier according to the invention has at least one opening that permits access of the EASI through membrane (C) to sensing area (A) while physically (i.e. bodily or mechanically) restricting such access to a limited portion of the sensing area. The significance of criterion(D-4) will be better understood when considered in connection with criterion (D-5) requiring that the limited portion of the electrode sensing area be topically defined with relation to the working electrode and the barrier layer so that the limited portion is within, or enclosed by, a circumjacent margin (also termed "margin D-5") having (a) an outer periphery defined by the periphery of the sensing area (A); "defined by" in this context means "having substantially the same shape as and substantially coinciding with" the sensing area (A) periphery; for example, when the sensing area (A) is circular, the outer periphery of margin (D-5) will also be circular and have the same diameter and the same center as the sensing area (A); however, sensing area (A) might have another geometrical shape in which case the outer periphery of margin (D-5) will have the same shape, the same dimensions, and the same topical position as the sensing area (A); hence, the projection of the outer periphery of margin (D-5) onto sensing area (A) must coincide topically with the periphery of sensing area (A).

Further requirements of criterin (D-5) are:

(b) an inner periphery distanced from the above discussed outer periphery (a), and (c) a width defined by the smallest distance between outer periphery (a) and inner periphery (b).

(D-6) The minimum width (D-5c) of margin (D-5) is an essential feature of the invention: because of the previously discussed features (D-1) through (D-4), margin (D-5) determines a well-defined and "endless" circumjacent stratiform portion or "loop" of electrolyte film (B) around the residual "open" portion of film (B) and the at least one opening (D-4), or any number of such openings, must be within such loop in order to ascertain that any undesired lateral diffusion of EASI into, or out of, electrolyte film (B) can be prevented safely.

As explained in more detail below, the minimum width of margin (D-5) will be:

(a) at least three times greater than the thickness of electrolyte film (B) when the barrier layer (D-1) is an "internal barrier" according to the invention as explained above, i.e. arranged intermediate membrane (C) and electrolyte film (B).

On the other hand, with an "external" barrier according to the invention, the minimum width of margin (D-5) will be (b) at least three times greater than the thickness of membrane (C) when membrane (C) is interposed between barrier layer (D-1) and electrolyte film (B).

In other words, the circumjacent margin (D-5) is a closed stratiform loop of electrolyte film situated "below", i.e. immediately adjacent the internally covering or "masking" barrier layer or immediately adjacent a membrane portion which, in turn, is covered or "masked" by the barrier layer, and on top of sensing area (A) depending upon whether the barrier layer or "mask" is "internal" or "external".

When using a barrier layer (D-1) with but a single opening (D-4), the periphery or edge of such opening may "coincide" in the sense explained above (i.e. projected onto sensing area A) with the inner periphery (b) of margin (D-5), or might be smaller but in no case must extend into the minimum width area of margin (D-5).

When, on the other hand, using a barrier layer (D-1) with a plurality (two, three or more) openings (D-4), the periphery or edge of any such opening must not extend into the minimum width area of margin (D-5). Preferably, the margin surrounding each opening should also have a minimum width satisfying the same criteria as margin (D-5).

For example, with the generally preferred circular periphery of sensing area (A) the outer periphery (a) of margin (D-5) will, of course, be circular as well, and the required minimum width (D-6) of margin (D-5) will most simply be obtained when the inner periphery (b) of margin (D-5) is circular as well, is coaxial or concentric with (D-5a), and is distanced from the latter by the minimum width or distance required by criterion (D-6); now, as long as the at least one opening is situated within the inner periphery (b) of margin (D-5), any EASI that permeates through the unmasked portion of membrane (C) on top of area (A) would have to migrate through the electrolyte film within circumjacent margin (D-5) before reaching the periphery of sensing area (A); the minimum length of this migration path is the width (D-5c) and the latter, in turn, has the minimum value defined by criterion (D-6). Now, since this migration path still extends through electrolyte film on top of sensing area (A)—i.e. in its "masked" portion-EASI react with the adjacent portion of the sensing electrode; the probability of such reaction increases with the length of the masked migration path and the minimum width requirements of criterion (D-6) are such that the probability of reaction is approaching unity.

Assuming, as an example, a circular sensing area (A), a circular and concentric inner periphery (D-5b), a typical film thickness of about 10 μm and a typical membrane thickness of 20 μm, an internal barrier would require a minimum margin width (D-6a) of 30 μm while an external barrier would require a minimum margin width (D-6b) of 60 μm.

Accordingly, a barrier layer (D-1) having a single circular and concentric opening with an inner diameter that is about 150 μm smaller than the diameter of sensing area (A) will provide an effective physical permeation barrier according to the invention suitable for either external or internal masking and preventing that any EASI that has passed through membrane (C) within the unmasked portion adjacent sensing area (A) will be prevented from lateral diffusion beyond the periphery of the sensing area.

Obviously, EASI could still reach electrolyte portions remote from the electrolyte film on top of sensing area (A), i.e. because the membrane-covered sensing face of the cell is greater than the sensing area (A) of the working electrode or/and if EASI could diffuse or permeate through the cell jacket.

Generally, it is assumed to be sufficient that the path of the EASI from the ambient medium or sample around the outside of the barrier layer to the sensing electrode should be long in comparison with the direct path from the sample through the membrane to the sensing electrode. However, according to a preferred embodiment of the MEAC according to the invention, the barrier layer will extend over the entire sensing face in physical contact with the membrane, on the one hand, and will be sealingly connected with the cell-supporting jacket, on the other hand. The jacket, in turn, will preferably be made of a material that is substantially impermeable to the EASI and is constructed free of joints that would permit diffusion of EASI.

Further, while the MEAC of the invention does not normally require a guard electrode, use of such an additional electrode may be desirable, and is encompassed by the invention for specific uses where an additional safeguard against lateral diffusion from the electrolyte space adjacent the film on sensing area into that film is desired.

BRIEF DESCRIPTION OF THE DRAWINGS

The invention will be better understood and objects other than those set forth above will become apparent when consideration is given to the following detailed description. Such description makes reference to the annexed drawings which illustrate the diagram of a prior art MEAC with a guard electrode for purposes of comparison with the invention as well as exemplary embodiments of the invention and wherein.

DETAILED DESCRIPTION OF THE PREFERRED EMBODIMENTS

Figure 1:
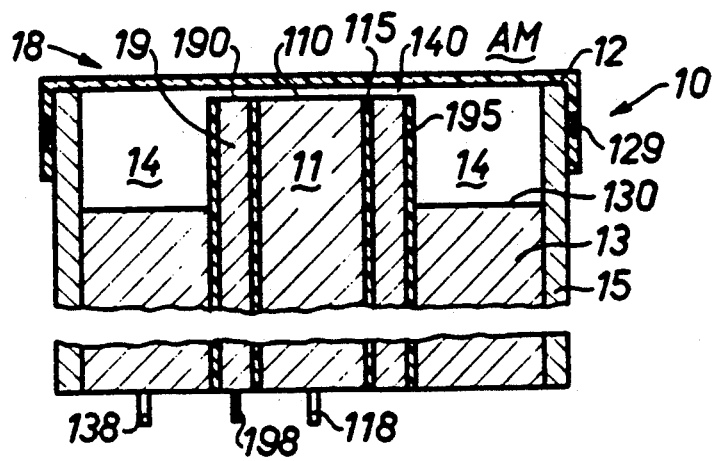
FIG. 1 is a diagrammatic sectional view of a prior art MEAC having an additional electrode functioning as an electric guard against unwanted contributions to the measuring current.

Describing now the drawings, FIG. 1 shows a prior art MEAC of the type disclosed in published British Application No. 2,013,895 in a diagrammatic and partially broken away sectional view.

MEAC 10 has a generally cylindrical and elongated body (only upper and lower end shown) that includes, in a generally coaxial form, a centrally arranged working electrode 11 having an electrolyte-exposed surface 110, a tubular guard electrode 19 having an electrolyte-exposed surface 190, and a counter electrode 13 having an electrolyte-exposed surface 130; insulating layers 115, 195 are arranged between adjacent surfaces of electrodes 11, 19, 13 and leads 118, 198, 138 are arranged for electrical connection of each electrode with a measuring circuit (not shown). It is to be noted that the presentation of FIG. 1 (and of FIGS. 2 and 3) is diagrammatic and should by no means imply that each electrode is a massive body nor that it extends through the entire probe body; in actual practice, the electrode surfaces 110, 130 and 190 in contact with electrolyte 14, and notably the surfaces 110, 190 are essential but neither sensing electrode 11 nor guard 19 need to have a substantial mass; for analytical operation, the surface area of a sensing electrode should generally remain as constant as possible and should neither decrease, e.g. due to deposits, nor increase, e.g. due to diffusion of electrolyte into the interface between electrode 11 and the adjacent insulator layer 115 separating that electrode from the adjacent electrode which in FIG. 1 is the guard electrode 19 but could be the counter electrode 23 or 33 as in FIGS. 2 and 3.

The counter electrode 13 of FIG. 1 is, in turn, electrically insulated against the guard electrode 19 by insulating layer 195. An EASI-impermeable jacket 15 of an insulating material or made of an electrically conducting material but provided with an additional insulator (not shown) against counter electrode 13, defines the probe or cell body that maintains the sensing surface 18 of cell 10 exposed to a sample of interest containing the EASI. A holding means 129, e.g. a dye ring as disclosed in U.S. Pat. No. 4,325,797, is used to sealingly connect semipermeable membrane 12 with jacket 15 and to retain a liquid and generally aqueous (acid, alkaline or neutral, optionally buffered) electrolyte 14 in contact with surface 130 of counter electrode 13 and extending as a thin liquid film 140 typically having a thickness of from 5 to 20 μm through the area defined by the inner surface of membrane 12 and the adjacent surfaces 110, 190 of sensing electrode 11 and guard 19.

The EASI may penetrate through membrane 12 into electrolyte film 140 but also into electrolyte 14 on top of counter electrode 13. However, because guard electrode 19 is maintained substantially at the same potential as working electrode 11, any EASI that has permeated or diffused into a portion of electrolyte 14 that is not the thin film layer 40 cannot diffuse "laterally" into electrolyte film 140 on top of working electrode surface 110 because prior to arriving there it would be "captured" by guard electrode surface 190, if the electrolyte film 140 on top of surface 190 has a suitable thickness/length ratio as defined in the above mentioned British Application.

Accordingly, it will be understood that guard electrode surface 190 and the electrolyte film covering that surface act as an electric guard or barrier which protects the sensing surface 110 against EASI that could reach it but by lateral diffusion through electrolyte film 140, i.e. in a radial direction.

When using MEACs with an electric guard or barrier as just explained for hydrogen determination as disclosed in U.S. Ser. No. 493,316 it was found that the insulator 115 between working electrode 11 and guard 19 may become an undesirable reservoir for EASI which if soluble in the insulator material may accumulate therein. When operating in a steady state this EASI reservoir may not become apparent; however, upon a step change of EASI concentration in the sample adjacent the sensing face of MEACs it will take an appreciable period of time for the EASI reservoir in insulator 115 to become depleted (thus generating a decaying residual current), or filled up to capacity (thus generating a slowly increasing contribution to the total current) and in either case delaying appearance of the true signal.

Surprisingly, it has been found according to the invention that a simple mechanical barrier arranged between the sample and the sensing area of the working electrode will avoid this disadvantage of prior art MEACs with a guard electrode and provide additional advantages including simplified structure and operation, and additional benefits, such as avoiding diffusion of gaseous or liquid components not related to the EASI from the MEAC into the ambient medium or vice-versa, and avoidance of measurement errors due to concentration polarization or local depletion of EASI in the sample.

According to a first general embodiment of the invention, the permeation barrier 26 of MEAC 20 will be arranged between the ambient medium AM (or sample) and the semipermeable membrane 22 to provide an "external" barrier or "mask".

Again, the overall construction of MEAC 20 is cylindrical and the working electrode 21 is coaxial with jacket 25 which is substantially impermeable to EASI; the sensing face 28, i.e. a generally circular front face of MEAC 20, is covered by membrane 22 which is sealingly connected with jacket 25 by means of a holding ring 229 in the manner discussed above.

According to the invention, MEAC 20 is provided with a physical permeation barrier in the form of a circular layer 26 made of a substantially inert solid material, e.g. stainless steel or another inorganic or organic material, which in a thickness of typically in the range of from about 50 μm to about 2000 μm will be substantially impermeable to diffusion of the EASI.

Stainless steel and similar metal barrier layers are preferred for external barriers because they will be substantially impermeable to all EASI of practical interest including hydrogen when used at a layer thickness within the 50 to 2000 μm range. Generally, barrier layer 26 is disposed in a substantially parallel configuration with membrane 22 and is in physical, i.e. bodily surface contact with the latter; a gauge of 0.1 to 0.3 mm is preferred.

To achieve or maintain such contact, a generally circular bracket member 27 of an inert material, such as a metal, e.g. stainless steel, bronze, or a ceramic material, a polymer material optionally reinforced, mineral glass, or the like, may be used to hold layer 26 in contact with membrane 22. A sealing ring 271 may be arranged between bracket 27 and barrier layer 26, and a clamp portion 272, thread, or the like securing element is provided at the lower end of bracket 27 to engage with a matching recess 252, thread, ring or the like retaining member of jacket 25.

When using a metal disc or the like rigid material for layer 26 it is preferred that the upper surface 220 of membrane 22 acts as a seal so that the pressure exerted by bracket 27 upon barrier layer 26 presses the latter upon membrane 22 to prevent the probe medium containing the EASI from penetrating into the barrier/membrane interface. Further, it is preferred for many purposes of MEAC 20 with an external barrier that barrier 26 be also in sealing engagement with jacket 22.

Figure 2:
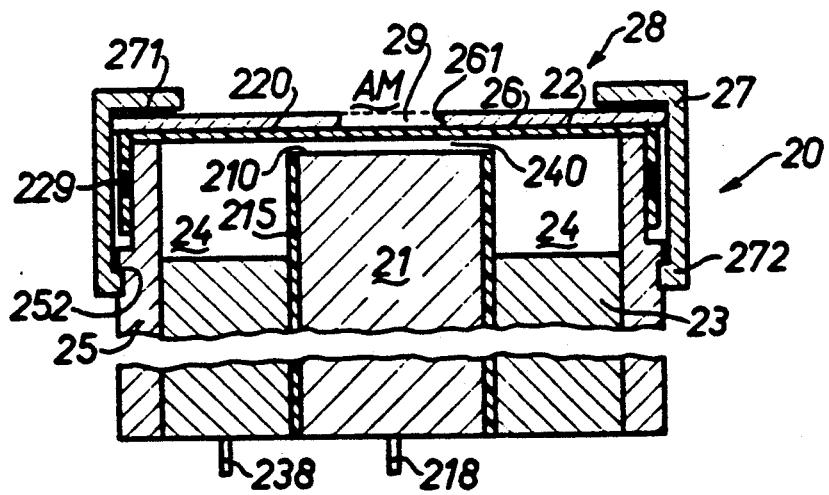
FIG. 2 is a diagrammatic sectional view of a MEAC having an external barrier layer in accordance with a first general embodiment of the invention.

The sensing area (A) of working electrode 21 in the general embodiment of FIG. 2 is the electrode surface 210 defined, for example, by an insulator 215 that provides for electrical separation of working electrode 21 and counter electrode 23; preferably, the electrode/insulator assemblies are made in accordance with the teachings of applicants' U.S. Pat. No. 4,096,047 (valve/valve seat structures). Leads 218, 238 serve to connect the respective electrodes 21, 23 with the measuring circuit (not shown).

A thin film 240 of liquid, e.g. aqueous, electrolyte covers the sensing area 210 and is in electrolytic contact with the counter electrode 23 because film 240 is in contact with the main electrolyte body 24 or the electrolyte reservoir. Generally, the thickness of electrolyte film 240 will be determined by the cell components that form the bodily structure of sensing face 28, and by membrane 22. Normally, such thickness will be in the range between 1 and 20 μm and can be measured by conventional means such as a light-splitting microscope. Barrier layer 26 is provided with a single circular opening arranged concentrically with the sensing area 210 of the working electrode.

In order to ascertain electrolyte contact between electrolyte film 240 and electrolyte main body 24, the inner edge 261 of layer 26 should not partition the inner circular area of electrolyte film 240 from the adjacent annular peripheral electrolyte film area that is covered by barrier layer 26; typically, the contact pressure exerted by edge 261 onto membrane 22 should not exceed an upper limit of about 3 bar; the lower pressure limit is not critical as long as diffusion of EASI into the membrane/barrier interface of the MEAC having an external barrier or mask is prevented. Another means to prevent such diffusion is to provide an intermediate layer of an adhesive material at the interface.

Barrier layer 26 may be made, of course, from other materials than the normally preferred stainless steel; metals are frequently preferred but other inorganic as well as organic materials providing a sufficient degree of impermeability to the EASI and being substantially inert under the conditions of their use in the MEAC are suitable including composite materials, such as gold-coated steel or polymer-coated metal.

With an external barrier it is important that the interface of barrier layer 26 and membrane surface 220 is sealed against diffusion of EASI into that interface; while a pressure sealing engagement of a metal layer 26 with polymer membrane 22 is preferred, sealingly effective intermediary layers formed of an adhesive, e.g. an epoxy resin, or another diffusion-blocking material may be used in addition to, or instead of, the pressure seal.

Further, while barrier layer 26 in the form of discrete and re-usable components of inventive MEACs are preferred, barrier layers may be obtained by electrodeposition, vacuum deposition or equivalent methods of applying inert material or metal, e.g. a noble metal or nickel, onto a polymer or equivalent substrate that may be, but need not be, the semipermeable membrane of the MEAC. Dimension, shape, function and number of the at least one opening (D-4) will be explained in connection with FIGS. 4 to 6, it being noted, however, that while only a single opening is shown in FIGS. 2 and 3, such single opening might be replaced by a plurality of smaller or even minute openings distributed in a preferably uniform manner within the area occupied by the openings 29 or 39 in FIGS. 2 and 3.

According to a preferred embodiment the inventive MEAC is provided with an external barrier formed by a circular sheet or disc 26 of an inert metal with a concentric opening defined by an edge 261; further, the outer periphery of disc 26 is sealingly connected with cell jacket 25, and edge 261 is sealingly connected with membrane 20; then, the entire cell 20 will be effectively shielded against EASI except at the sensing electrode portion beneath the opening.

Figure 3:
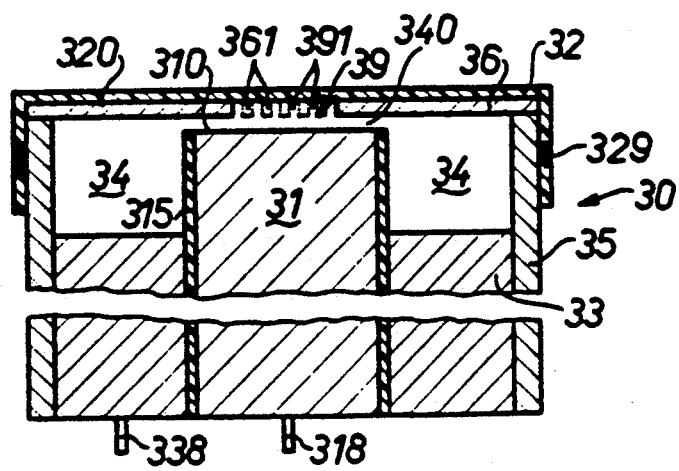
FIG. 3 is a diagrammatic sectional view of a MEAC having an internal barrier layer in accordance with a second general embodiment of the invention.

FIG. 3 represents a second general embodiment of the invention in the form of a MEAC 30 in which barrier layer 36 is intermediate the semipermeable membrane 32 and the sensing area 310 of working electrode 31 thus forming an "internal" barrier or mask according to the invention.

The structure of MEAC 30 of FIG. 3 is generally the same as that of MEAC 20 shown in FIG. 2; measuring electrode 31 has a circular sensing area defined by its electrolyte-contacting electrode surface 310 and adjacent insulator 315 which, in turn, provides for electrical separation of working electrode 31 and counter electrode 33; leads 318, 338 are for connection of the electrodes 31, 33 with a measuring circuit (not shown). Either MEAC of FIGS. 2 and 3 may have an additional guard electrode as explained in FIG. 1 but this is not normally preferred.

Again, membrane 32 is sealingly connected with jacket 35 by a holding ring 329. When the barrier layer of an inventive MEAC is arranged as an internal barrier it is essential that at least its surface next to the working electrode is made of an electrically insulating material, such as an organic polymer. While barrier layer 36 might consist e.g. of a polymer-coated metal disc, it is preferred for many purposes of the invention to use a polymer layer, e.g. a film of an organic polymer, as the barrier layer 36 for an internal mask.

Similarly as explained for MEAC 20 selection of material and thickness of layer 36 in a MEAC 30 will be such as to provide for a barrier that is inert to the electrolyte at the conditions of MEAC operation and substantially impermeable to the EASI as defined above; again, barrier layer 36 will be disposed in a substantially parallel configuration with the semipermeable membrane 32 and be in physical contact therewith; however, a particular sealing quality of the membrane/barrier interface 320 is not critical with an internal mask because EASI that diffuse into that interface would still not have access to the electrolyte layer 340 on top of sensing area 310. If barrier 36 is a film of a flexible organic polymer material it can be substantially contiguous with membrane 32, extend to the outer surface of jacket 35, and be sealingly connected with the jacket by means of the same holding ring 329 that also serves to secure membrane 32.

Again, an adhesive may be used at the interface 320 but this is not critical; alternatively, barrier layer 36 may be integrally connected with the semipermeable membrane 32, e.g. by means of an epoxy glue. When using a polymer material for the barrier layer 26 or 36, various materials may be used and the following Table I is given to show permeabilities of some non-limiting examples of polymers for use in a barrier layer (D-1) according to the invention. Generally, the thickness of an internally arranged barrier layer 36 should be as small as possible, preferably within the range of from 10 to 300 μm, a range of from 10 to 50 μm being even more preferred and commercially available film materials may be suitable.

With an internal barrier layer 36 arrangement as shown in FIG. 3, the at least one opening of the barrier is between the semipermeable membrane 32 and the electrolyte layer 340 on top of the sensing area; accordingly, the electrolyte layer between membrane 32 and sensing area 310 may be somewhat thicker than in the case of externally arranged barrier layer 36; in a preferred embodiment of the invention, the at least one opening 39 shown in full lines in FIG. 3 of barrier layer 36 is replaced by a number of smaller openings 391 separated from each other by bridge areas 361 shown in FIG. 3 in broken lines.

TABLE I

| Material | Permeability (n mole · μm · m$^{-2}$ · Pa$^{-1}$ · sec$^{-1}$) | | |
|---|---|---|---|
| | H$_2$ | O$_2$ | CO$_2$ |
| PVDC[1] | 0.069 | 0.002 | (not measured) |
| PVF[2] | 0.1 | 0.0065 | 0.022 |
| E-CTFE[3] | 0.15 | 0.05 | 0.22 |
| PETP[4] | 0.16 | 0.022 | 0.025 |
| PVC[5] | 0.36 | 0.01 | 0.04 |
| ETFE[6] | 1.5 | 0.2 | 0.5 |
| FEP[7] | 4 | 1.5 | 3.4 |

TABLE I-continued

| Material | Permeability (n mole · μm · m$^{-2}$ · Pa$^{-1}$ · sec$^{-1}$) | | |
|---|---|---|---|
| | H$_2$ | O$_2$ | CO$_2$ |
| PFA[8] | 5.6 | 2.2 | (not measured) |

[1] polyvinylidene chloride (e.g. SARAN, reg. trademark)
[2] polyvinyl fluoride (e.g. TEDLAR, reg. trademark)
[3] copolymer of ethylene and monochloro trifluoro ethylene (e.g. HALAR, reg. trademark)
[4] polyethylene terephthalate (e.g. MYLAR reg. trademark)
[5] polyvinyl chloride (e.g. HOSTALIT, reg. trademark, type "S")
[6] ethylene tetrafluoro ethylene copolymer (e.g. TEFZEL, reg. trademark)
[7] fluorinated ethylene/propylene (e.g. TEFLON, trade name)
[8] polyfluoro alkoxy polymer (e.g. TEFLON, trade name)

Figure 4:
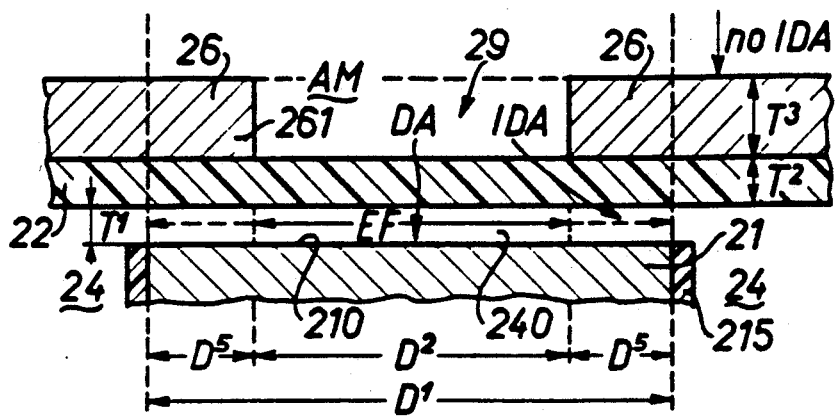
FIG. 4 is an enlarged view of the sensing area portion of the inventive MEAC shown in FIG. 2.
Figure 5:
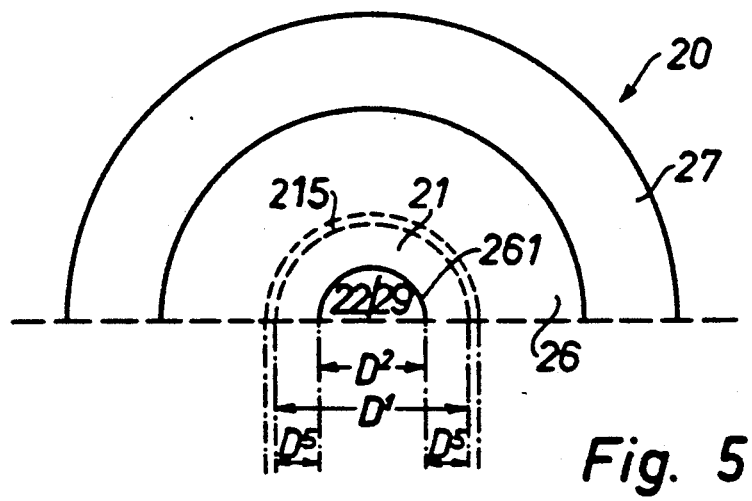
FIG. 5 is a diagrammatic top view of the sensing surface of the inventive MEAC shown in FIG. 2.

FIG. 4 is meant to further illustrate features (D-5) and of the inventive MEAC, i.e. arrangement and definition of the circumjacent margin around the at least one opening of the barrier layer.

While FIG. 4 shows a diagrammatic sectional view of the relevant area of an external mask, it will be understood that the important parameters of the size and position of the opening (D-4) are to be observed for internal masks as well, the main difference being the different minimum width of the circumjacent margin specified in feature (D-6).

FIG. 4 shows an enlarged portion of FIG. 2; working electrode 21 has a sensing area (A) defined by its electrolyte-exposed circular top surface 210 limited by adjacent insulator 215.

Barrier layer 26 between the ambient medium AM and membrane 22 has a single central opening 29 defined by barrier edge 261. As will be apparent from FIG. 5 (showing MEAC 20 of FIG. 2 in top view), edge 261 circumscribes a circular opening 29 that defines the limited portion of "direct access" to the electrolyte film 240 (double arrow EF; portion in full lines) as distinguished from the mask-covered part or "getter portion" of electrolyte film 240 on top of surface 210 covered by barrier layer 26 (double arrow EF; portion in broken lines); because of the generally preferred embodiment of concentric or coaxial arrangements of a circular sensing area 210 and a circular opening 29, the getter portion of electrolyte film 240 will have an annular shape and a width $D^5$ [$D^5 = \frac{1}{2}(D^1 - D^2)$].

According to the invention, the area of indirect access (IDA; curved arrow) of an EASI from ambient medium AM to the masked annular electrolyte film 240 on top of sensing area 210 has to meet the dimensional requirements of feature (D-6): with an external barrier or mask (as exemplified in FIGS. 2 and 4) EASI may permeate "laterally" (i.e. in a generally radial direction towards the end of the getter portion limited by the periphery of sensing area 210) immediately after having passed thickness $T^3$ of barrier layer 26 because membrane 22 is permeable to the EASI; thus, lateral permeation of EASI is possible both within the membrane and the electrolyte layer. Now, according to the invention, the length of the getter area (=the annular dimension $D^5$) must satisfy criterion (D-6), i.e. the minimum width of the circumjacent margin (=minimum width $D^5$ of annular getter area) must be at least three times greater than the thickness $T^2$ of membrane 22.

With an internal mask as explained for MEAC 30 in FIG. 3, any lateral diffusion of EASI within membrane (32) or within the barrier/membrane interface 320) cannot contribute to lateral EASI diffusion within electrolyte layer 340 toward the periphery of working electrode 31; now, since the membrane thickness is not a parameter of lateral EASI diffusion, the minimum width of the circumjacent margin (e.g. an annular getter area of film 340) must be at least three times greater than thickness $T^1$ of the electrolyte film where it has a substantially uniform thickness, i.e. between the surface 210, 310 of the working electrode 21, 31 and the next adjacent solid surface which, with an internal barrier layer, is the "lower" surface of that layer; in other words, the thickness of the barrier layer and the axial "length" of the at least one opening 39 or the several openings 391 is/are not considered to be part of the uniform thickness portion of electrolyte film 340.

The dimension requirement (D-6) is due to a theory developed in the course of arriving at the present invention: in order that the probability that all laterally diffusing EASI are caught by the working electrode in the indirectly accessible or masked getter portion of the sensing area (A) approaches unity, the length of the shortest EASI path through the getter portion must be at least three times greater than a diffusion parameter dependent upon the diffusion rate of an EASI within an electrolyte film adjacent the working electrode surface of a MEAC; since this diffusion rate will be greater in the liquid electrolyte than in a semipermeable membrane, and since electrolyte film thickness will generally not be larger than the membrane thickness, tripling of the membrane-related thickness parameter for an external mask will be about equal, in effect, to tripling the electrolyte-film-related thickness parameter.

If the radial length of the minimum getter path (=minimum radial width of circumjacent margin) is significantly less than three times the membrane thickness with an external mask, or significantly less than three times the thickness of the electrolyte film with an internal mask the probability that any laterally diffusing EASI are caught by the electrode in the masked area will be less than unity so that EASI may reach the insulator 215, 315 or the electrolyte reservoir 24, 34. This would give rise to the above discussed measurement errors caused by EASI diffusion into the electrolyte reservoir, or by the "well-function" of the insulator adjacent the working electrode.

On the other hand, there is no theoretical upper limit to the width of the circumjacent margin; practical considerations will, however, stand in the way of overly extending such width.

Turning back to FIG. 4, EASI from ambient medium AM have direct access (straight arrow DA) to the "unmasked" central circular portion of electrolyte film 240 only; this area of direct access is circular and has a diameter $D^2$ defined by edge 261 of opening 29. This diameter $D^2$ may, but need not, coincide with the inner periphery (D-5b) of the circumjacent margin (D-5); preferably, inner periphery (D-5b) does not coincide with $D^2$ but is within the masked area $D^5$ to provide for a safety margin to allow, at least, for normal deviations from ideal circularity and concentricity so that the actual length of a radial path through the getter area will be larger, e.g. by at least about 10%, preferably by at least about 30%, than the minimum width requirement defined by parameter (D-6) explained above.

Figure 6:
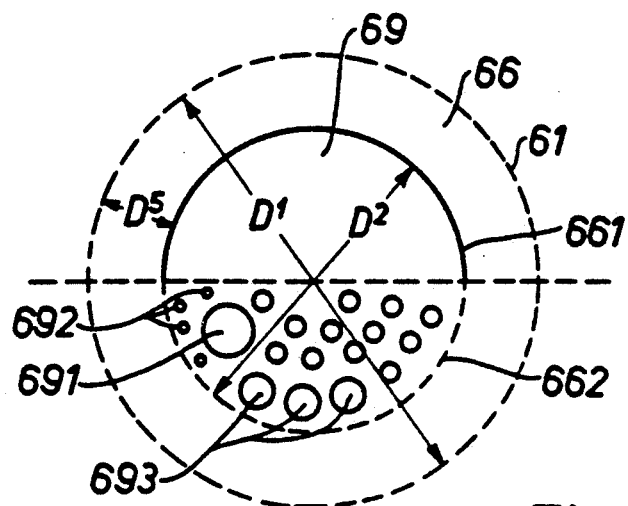
FIG. 6 is a diagrammatic top view illustrating various embodiments of openings in a barrier layer of a MEAC according to the invention.

FIG. 6 is an enlarged diagrammatic top view to further illustrate the width requirements of the circumjacent margin (D-5) in the preferred circular structure of the sensing area (A) having a barrier layer with a single concentric large opening 69 defined by edge 661 or a plurality of excentric smaller openings 691, 692, 693. The periphery 61 of sensing area (A) is shown in broken line as a circle of diameter $D^1$ and this coincides with the outer periphery (D-5a) of the circumjacent margin; the inner periphery (D-5b) is defined by a circle of diameter $D^2$ which, in the upper half of FIG. 6, coincides with edge 661 (full line) of a single concentric opening 69. In the lower half of FIG. 6, broken line 662 shows the position of the inner periphery (D-5b) that need not be a real line but can be a theoretical limit. The shape and the position of this limit defines the width (D-5c) of the circumjacent margin and any opening (D-4) of the barrier layer 66 must be within the area defined by this limit. While a single concentric opening, e.g. opening 69 or a smaller concentric opening, is preferred for some embodiments of the invention, a multiplicity of small or even many minute openings 692 are preferred for other embodiments: it has been found according to the invention that a barrier layer, notably an internal barrier, having a multiplicity of small holes within the area of direct access (i.e. within circumjacent margin D-5) has the added advantage that it can be used to reduce measuring errors caused by "concentration polarization", i.e. the effects of local depletion of EASI in the ambient medium adjacent the sensing face of the MEAC. Conventionally, these effects are reduced by mechanical stirring.

If an internal barrier according to a second general embodiment of the invention is provided with a multiplicity of small openings within the inner periphery of the circumjacent margin, this will not only prevent lateral diffusion of EASI but provide, in effect, for a multiplicity of minute sensing areas of the working electrode. If these areas are relatively small in proportion to the membrane thickness, a depletion zone within the membrane spreads in a "spherical" manner rather than in a "linear" manner. In consequence, the flux of EASI per membrane area unit is reduced and so is local depletion.

For this embodiment it is preferred that the internal barrier layer be as thin as possible, e.g. typically in the range of from 10 to 100 $\mu$m, and the diameters of the many small openings should be as small as is feasible in view of wettability; hole diameters could be in the general range of from 1 to 100 $\mu$m. Accordingly, wettable or even hydrophilic membrane materials may be preferred as long as swelling of the membrane does not interfere with the operation of the MEAC.

EXAMPLES

To illustrate operation of the MEAC according to the invention the following non-limiting examples are given.

EXAMPLE I

A commercially available hydrogen sensor (Orbisphere Laboratories, Geneva, Switzerland, Model 2230) having, in principel, the structure illustrated in FIG. 1 and including a platinum-coated circular working electrode (anode) of 6.32 mm diameter was operated in line with the method disclosed in the above mentioned U.S. Ser. No. 493,316 for detection of hydrogen as the EASI.

The electrolyte contained 45 g $CdF_2$ and 30 g of concentrated HF per liter of water and the membrane was a PVF membrane of 12.5 $\mu$m thickness.

The detector was transferred from water of room temperature containing dissolved elemental hydrogen at various concentrations (between 6 ppm and 1 ppb) to hydrogen-free water. The applied potential was 0.86V.

First, measurements were made without a barrier layer; response time in these instances at 25° C. were up to 280 minutes for a 90% change.

Secondly, the measurements were repeated with an external barrier layer 26 according to the invention made of a resiliently flexible flat disc of commercial grade stainless steel having a central opening of 6.0 mm diameter and a thickness of 0.2 mm; layer 26 was held by a bracket 27 of the type shown in FIG. 2 in sealing engagement with the jacket 25; under these conditions the response times at 25° C. were substantially improved, i.e. reduced to less than 3 minutes for a 90% change.

While a reduction of the response time could also be achieved by the electrical guard electrode, the results obtained with the structurally and operationally much simpler barrier layer 26 according to the invention were significantly better.

Further advantages observed with the MEAC comprising a steel sheet as external barrier layer 26 were elimination of loss of water from the electrolyte and of carbon dioxide absorption at prolonged operating periods.

EXAMPLE II

A MEAC for detection of oxygen as EASI dissolved in water as described in Example 1 of GB 2,013,895 (MEAC 10 with guard electrode 19 of the type shown in FIG. 1 herein) was operated as explained in detail in the British Specification, i.e. with an aqueous alkaline electrolyte (KOH in water) and a semipermeable membrane of FEP and having a thickness of 25.4 $\mu$m (1 mil). The cathode potential with respect to Ag/AgCl anode was minus 800 mV and a current of 1.6 $\mu$A per ppm of dissolved oxygen was observed at the working electrode (cathode) at 25° C. The diameter of the cathode was 6.32 mm.

When the cell was exposed to water free of oxygen, a residual current of about 8 nA flowed through the working electrode when the guard electrode was not operated but dropped to only about 0.8 nA as soon as the guard electrode was switched on (same potential as working electrode).

When the same MEAC was supplied with the steel disc and bracket described in the above Example I as an external mask sealingly engaged with the semipermeable membrane and the jacket as illustrated in FIG. 2 of the drawing herein, operation under the same conditions yielded a residual current of less than 0.8 nA regardless of whether or not the guard electrode was operated. In other words, the simple steel disc as a physical barrier had a "mechanical guard effect" that was at least equivalent to that of one of the best electrical guards currently available for oxygen sensors.

Again, the added advantage of prevention of water loss from the electrolyte and absence of carbon dioxide absorption by the electrolyte through the semipermeable membrane were observed.

Results similar to those described above in Examples I and II for external barrier layers were obtained when the external barrier layer of metal was replaced by an internal barrier layer in the form of a 20 $\mu$m film of PVDC that was substantially impermeable to the EASI in question. When the single central opening of the barrier used in Examples I and II was replaced by a multiplicity of holes (hole diameter about 50 $\mu$m; substantially uniform distribution of holes over the area of the central opening; distance between adjacent holes about 0.8 mm) similar effects as to prevention of lateral EASI diffusion, prevention of loss of water and lack of carbon dioxide absorption were observed. In addition, the MEAC was less sensitive against depletion phenomena in that substantially the same results were observed regardless of whether the sample solution was stirred or not.

Various modifications of the above disclosed embodiments of the invention will be apparent; for example, barrier layers may not only be combined with the semipermeable membrane to form barrier/membrane composites but it is within the ambit of the invention to use integral barrier/membrane structures, e.g. in the form of a substantially EASI-impermeable layer that is provided with a limited topical portion where the EASI but not the electrolyte may permeate.

While preferred embodiments of the present invention were shown and described above it is to be understood that the invention is not limited to such embodiments but may be embodied and practiced within the scope of the following claims.

ACCORDINGLY,

What I claim is:

1. A membrane-enclosed amperometric cell for use in determining the concentration of an electroactive species of interest in an ambient medium; said cell comprising:
   a working electrode having a sensing area defined by an essentially circular outer periphery;
   a film of a liquid electrolyte covering said sensing area and being in electrolytic contact with counter electrode, said film having a substantially uniform thickness;
   a polymer membrane that is substantially impermeable to said electrolyte but permeable to said electroactive species, said membrane extending in substantially conforming manner over said sensing area and said electrolyte film thereon, and said membrane having a substantially uniform thickness;
   a barrier layer that is substantially impermeable to said electroactive species and is arranged between said ambient medium and said sensing area;
   said barrier layer positioned between said ambient medium and said polymer membrane in sealing engagement with the latter;
   said barrier layer having at least one opening positioned relative to said sensing area so that direct access of said electroactive species to said sensing area is limited to a portion of said sensing area within an inner periphery that is coaxial with said outer periphery and together with the latter defines a circumjacent margin having a width that is at least three times greater than said thickness of said polymer membrane; said electrolyte film on said sensing area which confronts said barrier layer circumjacent margin being of a width and thickness that is effective to prevent lateral diffusion of said electroactive species through said electrolyte film beyond said circular outer periphery of said sensing area.

2. The cell of claim 1 wherein said barrier layer is a disk made of a resiliently flexible sheet of a substantially inert metal and wherein a holding means is provided to maintain said disk in said sealing engagement with said membrane as well as in a sealing engagement with a jacket containing said cell.

3. The cell of claim 2 wherein said disk is provided with a central circular opening positioned essentially coaxial with said sensing area.

4. The cell of claim 1 wherein said barrier layer is provided with a single and substantially circular opening positioned essentially coaxial with said sensing area.

* * * * *